Figure 1:
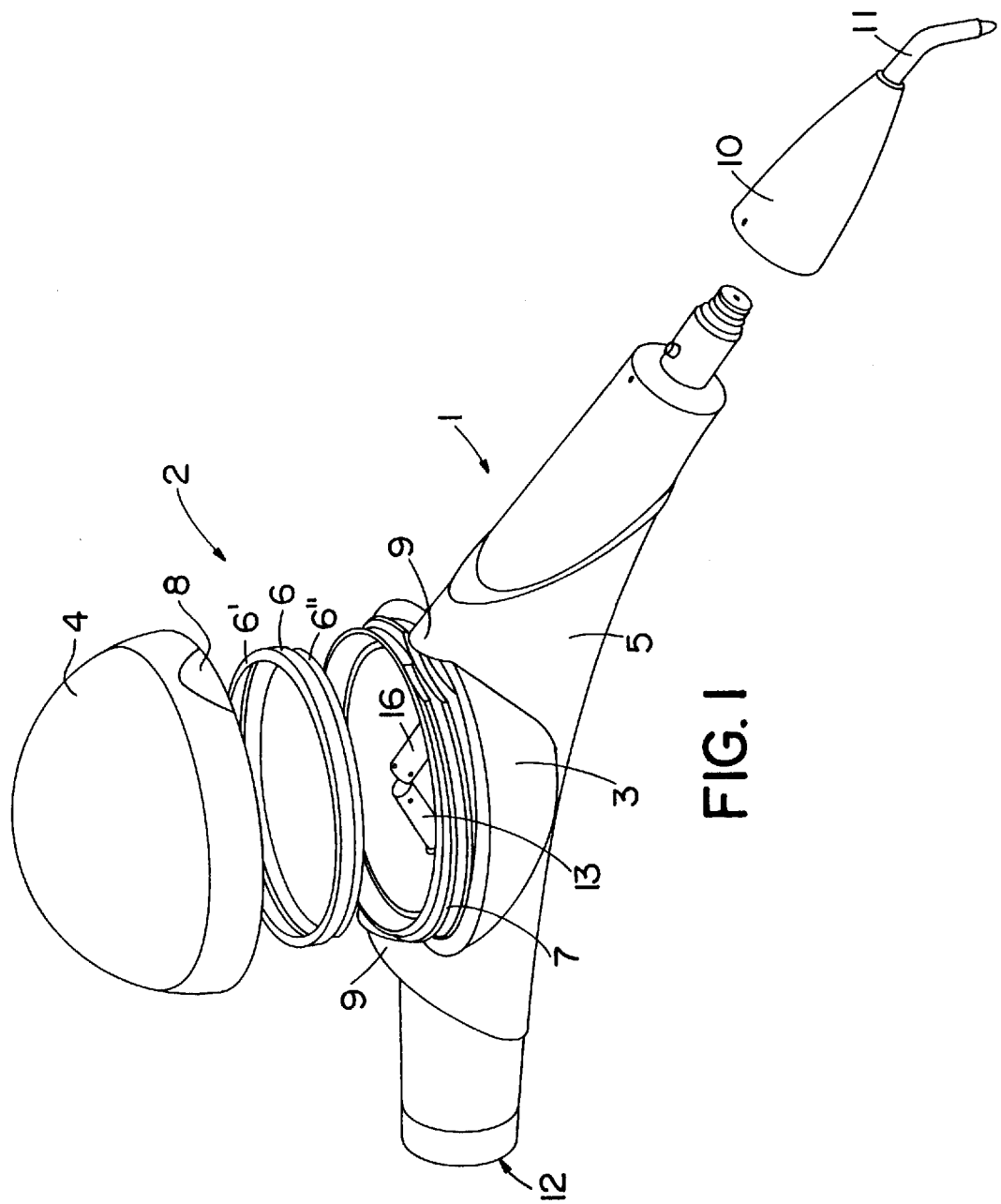

United States Patent [19]
Chavanne

[11] Patent Number: 5,857,851
[45] Date of Patent: Jan. 12, 1999

[54] DENTAL HANDPIECE

[75] Inventor: Philippe Chavanne, Aclens, Switzerland

[73] Assignee: Ferton Holding, Delemont, Switzerland

[21] Appl. No.: 49,694

[22] Filed: Mar. 27, 1998

[30] Foreign Application Priority Data

Apr. 7, 1997 [DE] Germany .................. 197 14 276.1

[51] Int. Cl.⁶ ................................................ A61C 3/02
[52] U.S. Cl. ............................................. 433/88; 451/102
[58] Field of Search ............................. 433/88; 451/90, 451/102

[56] References Cited

U.S. PATENT DOCUMENTS

| | | | |
|---|---|---|---|
| 1,398,527 | 11/1921 | Muspratt | 433/88 |
| 3,556,411 | 1/1971 | Nord et al. | 239/581.1 |
| 4,540,365 | 9/1985 | Nelson et al. | 433/88 |
| 4,648,840 | 3/1987 | Conger, Sr. | 433/125 |

*Primary Examiner*—John J. Wilson
*Attorney, Agent, or Firm*—Ratner & Prestia

[57] ABSTRACT

A dental handpiece for use with a prophylaxis treatment of carious teeth by means of a powder mixed with air and water is provided on a gripping sleeve of the handpiece with an integrated powder container which is formed as a closed hollow body of rotation. The hollow body of rotation forms a whirl chamber which spatially acts in all directions for a mixing of the stored powder with air which is supplied substantially in the geometric center of the body of rotation whereas the powder and air mixture which is formed in this powder container is transferred by means of a transfer line to a multiple nozzle arrangement of a spray head of the gripping sleeve via an inlet end of the transfer line which is provided also substantially in this geometric center directly adjacent to the outlet end of the flow line for air, the nozzle arrangement being also connected with a supply line for water.

14 Claims, 2 Drawing Sheets

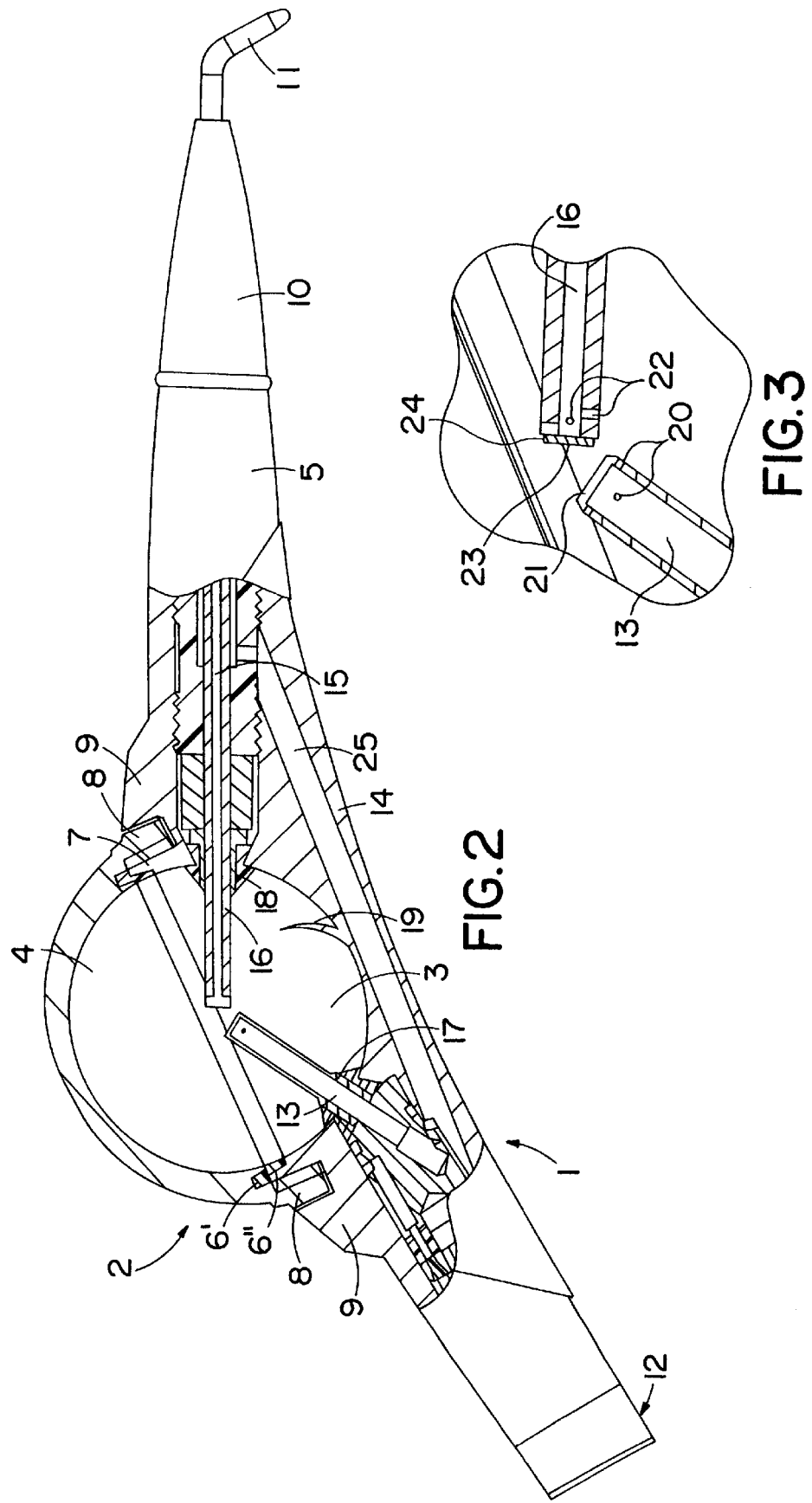

DENTAL HANDPIECE

TECHNICAL FIELD

The present invention relates to a dental handpiece for use with a prophylaxis treatment of carious teeth by means of a powder mixed with air and water.

BACKGROUND ART

U.S. Pat. No. 4,648,840 discloses a dental handpiece of the before mentioned kind which is provided at a backward end of a gripping sleeve or handle with an integrated powder container. This powder container stores a predetermined amount of powder as an abrasive material for the polishing or cleaning of teeth in the course of a singular treatment of teeth. The powder container is designed as a cylindrical pot or cannister the axis of which extends downwardly and substantially perpendicular to the axis of the gripping sleeve. This cylindrical cannister is provided on its open end with a screw connection for its connection with the gripping sleeve. The gripping sleeve is provided at this screw connection with the inlet end of a flow line for pressurized air and at a directly adjacent position with the outlet end of a transfer line for powder mixed with air. Both of these inlet and outlet ends are formed as connection bores of the respective flow and transfer lines whereby their axis extending in parallel to each other are both directed towards the bottom of the cannister. The powder and air mixture which is formed in the powder container is transferred via the transfer line to a multiple nozzle arrangement of a forward spray head of the handpiece. A supply line for water is also connected with this nozzle arrangement so that at the time of a tooth treatment a common delivery of the powder and air mixture together with water may be obtained. Supply of pressurized air in common with supply of water is obtained at the backward end of the gripping sleeve via a turbine in-line quick coupling of a supply connection for air and water of a standard dental unit as generally available in any dentist's office.

With the particular design of the powder container as a cylindrical cannister and further with the particular design of its connecting bores connected to the flow line for pressurized air and to the transfer line for powder mixed with air respectively there may be caused unfavorable mixing conditions within the powder container at the time of an actual tooth treatment. For avoiding any unnecessary disadvantages of the prophylaxis treatment the known handpiece therefore requires some increased skill of the dentist for his handling of such a handpiece whereby he also has to consider different specific gravity characteristics of the handpiece due to the arrangement of the powder container directly adjacent its turbine in-line quick coupling of the supply connection for air and water since such additional equipment is missing in other similar add-on dental instruments.

STATEMENT OF THE INVENTION & ADVANTAGES

The object of the present invention is to provide a dental handpiece for use with a prophylaxis treatment of carious teeth by means of a powder mixed with air and water which provides a less critical mixing of the powder that is stored in an integrated powder container of a gripping sleeve with pressurized air being supplied via a turbine in-line quick coupling to the inside of the container. Arrangements shall also be made for obtaining a greater freedom for the dentist for his handling of the handpiece during the period of a tooth treatment.

In accordance with the present invention a dental handpiece of the general kind as above described has an integrated powder container which is formed as a closed hollow body of rotation acting as a whirl chamber spatially in all directions. This hollow body of rotation further has outlet and inlet ends of a flow line for pressurized air and of a transfer line for a powder and air mixture respectively that are arranged substantially in the geometric center of such a hollow body of rotation in a mutually substantially adjacent arrangement.

Such a body of rotation as provided for the integrated powder container in accordance with the present invention provides flow conditions for the pressurized air within its cavity that are independent of any arbitrary gripping and handling of the handpiece and will therefore guarantee an optimum mixing of the air with the powder that is stored inside of this cavity. Such optimum flow conditions therefore also guarantee an invariable consistency of the formed powder and air mixture and secure at the same time its safe transfer to the multiple nozzle arrangement of the spray head of the handpiece.

As regards the mixing of the air with the powder optimum flow conditions for a nearly ideal whirl chamber will specifically be obtained with a design of the body of rotation in the form of a hollow sphere. Equally optimum flow conditions will also be obtainable, however, with a design of the body of rotation as a hollow ellipsoid of rotation having its main axis extending in the longitudinal direction of the gripping sleeve. In addition there may also be provided any suitable baffles for the cavity of the body of rotation which will favor the turbulence of the powder and air mixture prior to its transfer into the transfer line.

According to the present invention further improved conditions for the mixing of the air with the powder will be obtainable with an arrangement of the hollow body of rotation substantially at half-length of the gripping sleeve. Such an arrangement of the integrated powder container will then provide at the same time the actual gravity portion of the handpiece for allowing a well balanced arbitrary manipulation of the handpiece as required for any specifically desired tooth treatment. This will as well steadily secure optimum flow conditions for the mixing of the supplied pressurized air with the stored powder. The intended prophylaxis treatment may therefore be exercised with an optimum result.

DRAWING

Further features and advantages of the inventive dental handpiece may be derived from the following description of a preferred embodiment as schematically illustrated in the drawing.

FIG. 1 is a perspective view with a partwise exploded illustration of the handpiece having an integrated powder container in the form of a hollow sphere, FIG. 2 is a partwise sectioned general view of the handpiece and FIG. 3 is a sectional view of the outlet and the inlet ends as formed by tubular pieces of the supply line for pressurized air and of the transfer line for the powder and air mixture respectively of the handpiece of FIGS. 1 and 2.

As illustrated in FIG. 1 a dental handpiece 1 comprises an integrated powder container 2 which is designed as a closed hollow body of rotation in the form of a hollow sphere. This hollow sphere comprises two hemispheres 3 and 4. The one hemisphere 3 forms a first body portion of the hollow body of rotation and is fixedly connected to a handle or gripping sleeve 5 of the handpiece. This one body portion as illustrated in FIG. 2 preferably forms an integral portion of the housing or shell of the gripping sleeve 5.

The second hemisphere 4 forming a second body portion of the hollow body of rotation serves as a removable cover member which may be removably connected with the fixedly arranged hemisphere 3 of the gripping sleeve 5 together with an interposed sealing ring 6. The removable interconnection of the two hemispheres 3 and 4 is obtained by a quarter-turn fastener or bayonet catch 7 and as an alternative could be also obtained by a common screw connection.

The bayonet catch 7 is specifically designed such that after the hemisphere 4 serving as a cover member has been placed on the hemisphere 3 a relative rotation over an angle of for example about 100° will be necessary for transferring the hemisphere 4 from an opened position into a closed position. Whereas such a bayonet catch as such already provides a relatively safe closed position in respect to the inside pressure of the powder container which prevails when the pressurized air is supplied to its cavity the closed position of the hemisphere 4 could be additionally secured by providing two diametrically opposed cam-shaped elevations 8 on the one hemisphere 4 and cooperating with two corresponding recesses as provided on projections 9 of the housing of the gripping sleeve 5 in the manner of a snap connection which becomes active as soon as the hemisphere 4 has been brought into its closed position. This snap connection is at the same time designed such that for achieving its final position some back pressure must be overcome. Such back pressure enlarges the closing force of the bayonet catch 7 and accordingly improves the safety factor for the handling of the handpiece in regard to the actual pressure of the pressurized air.

The handpiece 1 is provided on the forward end of the gripping sleeve 5 with a removable spray head 10. This spray head 10 has a multiple nozzle arrangement 11 serving as a spray means for the powder and air mixture as formed in the powder container 2 in common with water which by means of a flow line that extends inside of the gripping sleeve is supplied at the same time to this nozzle arrangement. The pressurized air which is necessary for the mixing of the powder inside of the powder container 2 and the water are supplied via a turbine in-line quick coupling as connected to a supply connection for air and water whereby such a quick connection may for example be designed as described in DE 25 49 177 C3.

The design of the powder container 2 as a closed hollow body of rotation specifically in the form of a hollow sphere and arranged substantially in the gravity portion of the handpiece 1 results in almost ideal mixing conditions for the stored powder and the pressurized air. Such a hollow sphere could namely be considered in respect to its prevailing flow conditions as a whirl chamber which spatially acts in all directions. The specific flow conditions within the cavity of such a hollow sphere are primarily optimized by the provision that the pressurized air is supplied into the cavity of the hemisphere via a tubular piece 13 as illustrated in FIG. 2. This tubular piece 13 forms the outlet end of the supply line for pressurized air which by means of the before mentioned quick coupling is connected to the common supply connection for air and water which as it is believed known forms a standard dental unit as generally available in any dentist's office. The tubular piece 13 is inserted into a wall 14 of the one hemisphere 3 in such a manner that it is provided with an arrangement which substantially extends towards the center of the hollow sphere. The outlet end of the tubular piece 13 is on the other side provided with an arrangement directly adjacent the inlet end of a transfer line 15 which leads to the multiple nozzle arrangement 11 of the spray head 10. This inlet end of the transfer line 15 is as well provided with a tubular piece 16 which is also inserted into the wall 14 of the hemisphere 3. This wall 14 forms an integral portion of the housing or shell of the gripping sleeve 5. The tubular piece 16 also extends substantially towards the center of the hollow sphere or its cavity respectively for obtaining the substantially adjacent positioning of its inlet end at this very point.

The two tubular pieces 13 and 16 are each sealed on the hemisphere 3 by means of a packing 17 and 18 respectively. Each packing 17, 18 has two substantially cone-shaped sealing lips for obtaining an optimum sealing of the powder container. The one sealing lip which is arranged on the inner wall of the hollow sphere is obviously pressed against this inner wall of the one hemisphere 3 as caused by a deformation which occurs as soon as the pressurized air is supplied into the cavity of the hollow sphere via the tubular piece 13. Due to a deformation of this one sealing lip of each packing 17, 18 under the influence of the pressurized air an improved sealing of the respective tubular piece will be obtained in respect to its passage through the wall of the hemisphere 3 forming a portion of the housing of the gripping sleeve.

Some additional improvement for the sealing of the cavity of the hollow sphere as based more or less on the same principle of a deformation of the seal under the influence of the pressurized air is also obtained by the sealing ring 6. This sealing ring 6 is namely provided with two mutually offset sealing lips 6' and 6" of which the one sealing lip 6' projects into a circular crew of the cover member 4 and the second sealing lip 6" is in contact with an inner sealing rim of the hemisphere 3 the wall 14 of which forms a portion of the housing of the gripping sleeve 5. With such a design of the sealing ring 6 there will be obtained some squeezing of the one sealing lip 6' when the hemisphere 4 is fastened on the hemisphere 3 by means of the bayonet catch 7. Such squeezing of the sealing lip 6' will result in an increased pressure inside of the sealing ring 6 to thereby additionally improve the safety factor of the closed position of the bayonet catch 7. The increased inner pressure prevailing within the cavity of the hollow sphere when the pressurized air is supplied will on the other side also directly act against the second sealing lip 6" for its pressing against its sealing rim on the hemisphere 3 to thereby still further increase the sealing action of the sealing ring 6.

As may also be derived from the illustration in FIG. 2 it is shown that the two tubular pieces 13 and 16 are inclined with respect to each other under an angle of about 130° to 135°. With such a directional extension of the two tubular pieces optimum flow and mixing conditions will be obtained. within the cavity of the hollow sphere as soon as pressurized air is admitted via the tubular piece 13.

Such optimum conditions provide an intensive mixing of the pressurized air and the powder that is stored in the powder container. While already with the form as such provision is made by the hollow sphere for obtaining the action of a whirl chamber for the mixing of the pressurized air with the stored powder within its cavity, it should as well be understood that the turbulence of the powder and air mixture may be further improved by providing suitable baffles inside of the hollow sphere such as the baffle 19 which is integrally formed on the wall 14 of the hemisphere 3. Such baffles favor the spatial action in all directions of such a whirl chamber which could be further favored by providing the outlet end of the tubular piece 13 with a perforated belt of air outlet ports 20 upstream of an endside closure plate 21 as shown in FIG. 3. This closure plate 21 could be arranged at the end of the tubular piece 13 with a slight inclination under an angle of about 45° to 60° with respect to the axis of the tubular piece 13.

The mutually inclined arrangement of the two tubular pieces 13 and 16 also facilitates the transfer of the powder and air mixture towards the multiple nozzle arrangement 11 of the spray head 10 of the gripping sleeve 5. As also illustrated in FIG. 3 such transfer of the powder and air mixture could be improved by also providing a perforated belt of inlet ports 22 on the outlet end of the transfer line 15 as formed by the tubular piece 16 whereby these inlet ports 22 are provided upstream of a center bore 23 of an endside nozzle piece 24. For optimizing the flow conditions at the inlet end of the transfer line 15 the measure could be taken of allowing a relative adjustment of the two tubular pieces 13 and 16 between a contact position of the edges of the closure plate 21 and the nozzle piece 24 and a spaced apart position up to about 1.0 to 1.5 mm at the maximum. Such a mutual adjustability could be provided by a relatively adjustable arrangement of the two tubular pieces with respect to the wall 14 of the gripping sleeve 5. The wall 14 is further shown in FIG. 2 as having a bore 25 which finally forms a partial length of the supply line for water leading to the multiple nozzle arrangement 11 of the spray head 10. This supply line for water is as well connected by means of the above mentioned quick coupling to the supply connection for air and water.

For a practical embodiment of the handpiece there may be provided a supply of pressurized air under a pressure of about 2.5 to 3.0 bar and a flow rate of about 45 liter/minute together with a supply of water under a pressure of 1.8 bar both via the quick coupling. Such values provide a stream of the powder and air mixture which when sprayed against tooth surfaces will remove plaque and discolorations from the tooth surfaces for cleaning and polishing purposes of a tooth treatment.

For a singular treatment as intended by the use of the handpiece according to the present invention the hollow sphere may be provided with a volume of about 50 cm$^3$ and may be filled to about one third with the powder the main portion of which could be sodium bicarbonate or other abrasive particles having a particle size of about 100 microns at the maximum. Each outlet port 20 at the outlet end of the tubular piece 13 could then be provided with a diameter of about 0.4 mm whereas each inlet port 22, 23 at the inlet end of the tubular piece 16 could have a diameter of about 0.6 mm.

Finally it still should be mentioned that the powder container could as well be formed as a hollow ellipsoid of rotation the main axis of which then should extend in the longitudinal direction of the handpiece and its gripping sleeve respectively. For allowing a visual communication with the cavity of the powder container its removable cover member could comprise a transparent material. The size of the powder container would be finally dimensioned such that more or less only its cover member will be provided with a form projecting upwardly over the surrounding portions of the gripping sleeve.

I claim:

1. A dental handpiece for use with a prophylaxis treatment of carious teeth by means of a powder mixed with air and water, comprising a gripping sleeve;

a powder container as integrated with the gripping sleeve and storing a predetermined amount of powder;

a flow line for pressurized air connected to the powder container;

a transfer line for powder mixed with air connecting the powder container with a multiple nozzle arrangement at a forward spray head of the gripping sleeve, the transfer line having an inlet end on the side of the container and being arranged adjacent to an outlet end of the flow line for pressurized air;

a supply line for water connected to the multiple nozzle arrangement; and a coupling means of a turbine in-line quick coupling of a supply connection for air and water and provided at a backward end of the gripping sleeve; wherein the powder container is formed as a closed hollow body of rotation acting as a whirl chamber spatially in all directions, and the outlet end of the flow line for pressurized air and the inlet end of the transfer line for the powder and air mixture are arranged substantially in the geometric center of the hollow body of rotation.

2. A dental handpiece according to claim 1, wherein the hollow body of rotation is formed as a hollow sphere.

3. A dental handpiece according to claim 1, wherein the hollow body of rotation is formed as a hollow ellipsoid of rotation a main axis of which extends along a longitudinal direction of the gripping sleeve.

4. A dental handpiece according to claim 1, wherein the hollow body of rotation is arranged substantially at half length of the gripping sleeve for substantially serving as a gravity center of the handpiece.

5. A dental handpiece according to claim 1, wherein the hollow body of rotation is provided with inner baffles that will favor a turbulence of the power and air mixture.

6. A dental handpiece according to claim 1, wherein the hollow body of rotation comprises a first body portion which is fixedly connected to the gripping sleeve and a second body portion which is substantially equally sized and removably connected to the first body portion as a removable cover member.

7. A dental handpiece according to claim 6, wherein the cover member in connected to the first body portion by means of a bayonet catch having a closing position which is secured by means of a snap connection between the cover member and the gripping sleeve.

8. A dental handpiece according to claim 6, wherein a sealing ring is arranged between the cover member and the first body portion of the hollow body of rotation, the sealing ring comprising two mutually offset sealing lips of which a first sealing lip projects into an annular groove of the cover member as a compression and squeezer member and a second sealing lip is in sealing contact with an inner sealing rim of the first body portion.

9. A dental handpiece according to claim 6, wherein the first body member of the hollow body of rotation is integrally formed with a housing of the gripping sleeve whereby its wall is provided with a partial length of the supply line for water.

10. A dental handpiece according to claim 1, wherein the outlet end of the flow line for pressurized air and the inlet end of the transfer line for the powder and air mixture are formed with two tubular pieces which are arranged on the first body portion of the hollow body of rotation as projecting into its cavity and extending substantially towards its geometric center.

11. A dental handpiece according to claim 10, wherein the two tubular pieces are relatively adjustably arranged on the gripping sleeve.

12. A dental handpiece according to claim 10, wherein the tubular piece of the outlet end of the flow line for pressurized air comprises a perforated belt of air outlet ports upstream of an endside closure plate.

13. A dental handpiece according to claim 10, wherein the tubular piece of the inlet end of the transfer line for the powder and air mixture comprises a perforated belt of inlet ports downstream of an endside nozzle piece having a center inlet bore.

14. A dental handpiece according to claim 10, wherein the two tubular pieces are arranged with respect to each other at an angle of inclination of about 130° to 135° and are relatively adjustable with respect to each other between a mutual contact position of the edges of the closure plate and of the nozzle piece and a spaced apart position of about 1.0 to 1.5 mm at a maximum.

* * * * *